United States Patent [19]
Flick et al.

[11] Patent Number: 5,527,946
[45] Date of Patent: Jun. 18, 1996

[54] PREPARATION OF ALIPHATIC ALPHA, OMEGA-AMINONITRILES

[75] Inventors: Klemens Flick, Herxheim; Johann-Peter Melder, Mannheim; Werner Schnurr, Herxheim; Klaus Ebel, Lampertheim; Tom Witzel, Ludwigshafen; Wolfgang Harder, Weinheim; Alwin Rehfinger, Mutterstadt; Rolf Fischer, Heidelberg, all of Germany

[73] Assignee: BASF Aktiengesellschaft, Ludwigshafen, Germany

[21] Appl. No.: 375,573

[22] Filed: Jan. 18, 1995

[30] Foreign Application Priority Data

Dec. 27, 1994 [DE] Germany ................. 44 46 893.8

[51] Int. Cl.$^6$ ........................................ C07C 253/30
[52] U.S. Cl. ............................... 558/459; 558/452
[58] Field of Search ................................. 558/459

[56] References Cited

U.S. PATENT DOCUMENTS

| | | | |
|---|---|---|---|
| 2,208,598 | 10/1941 | Rigby | 558/459 |
| 2,257,814 | 7/1940 | Rigby | 558/459 |
| 5,151,543 | 9/1992 | Ziemecki | 558/459 |
| 5,296,628 | 3/1994 | Sanchez | 558/459 X |

FOREIGN PATENT DOCUMENTS

| | | |
|---|---|---|
| 0161419 | 11/1985 | European Pat. Off. . |
| 0848654 | 12/1951 | Germany . |
| 4235466 | 4/1994 | Germany . |
| 1325153 | 8/1973 | United Kingdom ........... 558/459 |
| WO92/21650 | 12/1992 | WIPO . |
| WO93/16034 | 8/1993 | WIPO . |

*Primary Examiner*—Joseph Paul Brust
*Attorney, Agent, or Firm*—Keil & Weinkauf

[57] ABSTRACT

Aliphatic alpha, omega-aminonitriles are prepared by partial hydrogenation of aliphatic alpha, omega-dinitriles at elevated temperatures and superatmospheric pressure in the presence of a solvent and of a catalyst by a process which comprises using a catalyst which (a) contains a compound based on a metal selected from the group consisting of nickel, cobalt, iron, ruthenium and rhodium and (b) contains from 0.01 to 25% by weight, based on (a), of a promoter based on a metal selected from the group consisting of palladium, platinum, iridium, osmium, copper, silver, gold, chromium, molybdenum, tungsten, manganese, rhenium, zinc, cadmium, lead, aluminum, tin, phosphorus, arsenic, antimony, bismuth and rare earth metals and (c) from 0 to 5% by weight, based on (a), of a compound based on an alkali metal or on an alkaline earth metal, with the proviso that the component (a) is not based on iron or iron and one of the metals selected from the group consisting of cobalt, ruthenium and rhodium when (b) is a promoter based on a metal selected from the group consisting of titanium, manganese, chromium and molybdenum, and with the further proviso that, when a compound based on only ruthenium or rhodium or ruthenium and rhodium or nickel and rhodium is selected as component (a), the promoter (b) may be dispensed with.

8 Claims, No Drawings

PREPARATION OF ALIPHATIC ALPHA, OMEGA-AMINONITRILES

The present invention relates to an improved process for the preparation of aliphatic alpha, omega-aminonitriles by partial hydrogenation of aliphatic alpha, omega-dinitriles at elevated temperature and superatmospheric pressure in the presence of a solvent and a catalyst.

WO 92/21650 describes the partial hydrogenation of adiponitrile to 6-aminocapronitrile in the presence of a Raney nickel catalyst and ammonia as a solvent in a yield of 60% at a conversion of 70%. 9% of hexamethylenediamine is formed as a by product. The disadvantage of this process is the short life of the catalyst.

U.S. Pat. Nos. 2,257,814 and 2,208,598 likewise describe preparation processes of 6-aminocapronitrile starting from adiponitrile, the catalysts used being Raney cobalt or iron, nickel and cobalt catalysts on various carriers. The fact that the selectivities of from 50 to 60% are too low for industrial applications is a disadvantage of these processes.

In the process of WO 93/16034, the yield of aminocapronitrile can be increased by hydrogenating adiponitrile in the presence of Raney nickel, of a base, such as sodium hydroxide, potassium hydroxide, lithium hydroxide or ammonium hydroxide, and of a transition metal complex containing, for example, iron, cobalt, chromium or tungsten as transition metals, and of a solvent. In this process, quantitative yields of aminocapronitrile are said to be obtained at conversions of from 45 to 60%. The disadvantage of this process is the working up of the generally toxic transition metal complexes from the reaction mixtures obtained.

EP-A 161,419 describes the partial hydrogenation of adiponitrile using a rhodium-containing catalyst on a magnesium oxide carrier. At a conversion of 70%, a selectivity of 94% is achieved. The disadvantage is the expensive preparation method of the Rh/MgO catalysts (cf. J. of Cat. 112 (1988), 145–156).

DE-A 4,235,466 describes the fixed-bed hydrogenation of adiponitrile to 6-aminocapronitrile over an iron sponge catalyst (unsupported catalyst) which was prepared from iron ore by a special method and subsequently doped with cobalt, titanium manganese chromium, molybdenum, ruthenium or iridium. Owing to the small surface area (0.8 m$^2$/g), these catalysts generally have useful activity only at high pressures and high temperatures. A further disadvantage of this process is the rapid loss of activity: in spite of a reduction in the adiponitrile and hydrogen loading, which leads to an increase in conversion, according to Example 7 the conversion decreased by 5% in the course of 24 hours.

DE-A 848,654 describes the continuous fixed-bed hydrogenation of adiponitrile over palladium on silica gel and over metals of the eighth group of the Periodic Table, these metals preferably being used in the form of spinels. A substantial disadvantage of these catalysts is their unsatisfactory life.

It is an object of the present invention to provide an improved process for the preparation of aliphatic alpha, omega-aminonitriles by partial hydrogenation of adiponitrile, which process does not have the abovementioned disadvantages; in particular, it is intended to provide a process in which the catalysts used have a longer life than those of the prior art.

We have found that this object is achieved by a process for the preparation of aliphatic alpha,omega-aminonitriles by partial hydrogenation of aliphatic alpha,omega-dinitriles at elevated temperatures and superatmospheric pressure in the presence of a solvent and of a catalyst, which comprises using a catalyst which (a) contains a compound based on a metal selected from the group consisting of nickel, cobalt, iron, ruthenium or rhodium and (b) contains from 0.01 to 25, preferably from 0.1 to 5%, by weight, based on (a), of a promoter based on a metal selected from the group consisting of palladium, platinum, iridium, osmium, iron, copper, silver, gold, chromium, molybdenum, tungsten, manganese, rhenium, zinc, cadmium, lead, aluminum, tin, phosphorus, arsenic, antimony, bismuth or rare earth metals and (c) from 0 to 5, preferably from 0.1 to 3%, by weight, based on (a), of a compound based on an alkali metal or on an alkaline earth metal.

Preferred catalysts are those in which the component (a) contains at least one compound based on a metal selected from the group consisting of nickel, cobalt and iron, in an amount of from 10 to 95% by weight, and ruthenium and/or rhodium in an amount of from 0.1 to 5% by weight, based in each case on the sum of the components (a) to (c), the component (b) contains at least one promoter based on a metal selected from the group consisting of silver, copper, manganese, rhenium, lead and phosphorus, in an amount of from 0.1 to 5% by weight, based on (a), and the component (c) contains at least one compound based on the alkali metals and alkaline earth metals selected from the group consisting of lithium, sodium, potassium, cesium, magnesium and calcium, in an amount of from 0.1 to 5% by weight.

Particularly preferred catalysts are:

catalyst A, containing 90% by weight of cobalt oxide (COO), 5% by weight of manganese oxide ($Mn_2O_3$), 3% by weight of phosphorus pentoxide and 2% by weight of sodium oxide ($Na_2O$), catalyst B, containing 20% by weight of cobalt oxide (COO), 5% by weight of manganese oxide ($Mn_2O_3$), 0.3% by weight of silver oxide ($Ag_2O$), 70% by weight of silica ($SiO_2$), 3.5% by weight of alumina ($Al_2O_3$), 0.5% by weight of iron oxide ($Fe_2O_3$), 0.5% by weight of magnesium oxide (MgO) and 0.5% by weight of calcium oxide (CaO), and catalyst C, containing 20% by weight of nickel oxide (NiO), 66.4% by weight of silica ($SiO_2$), 3.7% by weight of alumina ($Al_2O_3$), 0.8% by weight of iron oxide ($Fe_2O_3$), 0.76% by weight of magnesium oxide (MgO), 1.92% by weight of calcium oxide (CaO), 3.4% by weight of sodium oxide ($Na_2O$) and 2.0% by weight of potassium oxide ($K_2O$).

The catalysts which can be used according to the invention may be unsupported or supported catalysts. Examples of suitable carriers are porous oxides, such as alumina, silica, aluminosilicates, lanthanum oxide, titanium dioxide, zirconium dioxide, magnesium oxide, zinc oxide and zeolites, as well as active carbon or mixtures thereof.

As a rule, the preparation is carried out by precipitating precursors of the component (a) together with precursors of the promoters (components (b) and, if desired, with precursors of the trace components (c) in the presence or absence of carriers (depending on which catalyst type is desired), if desired processing the resulting catalyst precursor to give extrudates or pellets, drying the latter and then calcining them. Supported catalysts are also obtainable in general by impregnating the carrier with a solution of the components (a), (b) and, if desired, (c), where the individual components may be added simultaneously or in succession, or by spraying the components (a), (b) and, if desired, (c) onto the carrier by a method known per se.

Suitable precursors of the components (a) are as a rule readily water-soluble salts of the abovementioned metals, such as nitrates, chlorides, acetates, formates and sulfates, preferably nitrates.

Suitable precursors of the components (b) are as a rule readily water-soluble salts or complex salts of the abovementioned metals, such as nitrates, chlorides, acetates, formates and sulfates and in particular hexachloroplatinate, preferably nitrates and hexachloroplatinate.

Suitable precursors of the components (c) are as a rule readily water-soluble salts of the abovementioned alkali metals and alkaline earth metals, such as hydroxides, carbonates, nitrates, chlorides, acetates, formates and sulfates, preferably hydroxides and carbonates.

The precipitation is carried out in general from aqueous solutions, either by adding precipitating reagents or by changing the pH or the temperature.

The preliminary catalyst material thus obtained is usually dried, in general at from 80° to 150° C., preferably from 80° to 120° C.

Calcining is usually carried out at from 150° to 500° C., preferably from 200° to 450° C., in a gas stream comprising air or nitrogen.

After the calcination, the catalyst material obtained is generally exposed to a reducing atmosphere (activation), for example to a hydrogen atmosphere or a gas mixture containing hydrogen and an inert gas, such as nitrogen, for from 2 to 24 hours at from 80° to 250° C., preferably from 80° to 180° C., in the case of catalysts based on ruthenium or rhodium as component (a) or from 200° to 500° C., preferably from 250° to 400° C., in the case of catalysts based on a metal selected from the group consisting of nickel, cobalt and iron as component (a). The catalyst space velocity here is preferably 200 l per l of catalyst.

The activation of the catalyst is advantageously carried out directly in the synthesis reactor, since this usually dispenses with an otherwise necessary intermediate step, ie. the passivation of the surface at, usually, from 20° to 80° C., preferably from 25° to 35° C., by means of an oxygen/nitrogen mixture, such as air.

The activation of passivated catalysts is then preferably effected in the synthesis reactor at from 180° to 500° C., preferably from 200° to 350° C., in a hydrogen-containing atmosphere.

The catalysts may be used as fixed-bed catalysts by the liquid-phase or trickle-bed procedure or as suspension catalysts.

The starting materials used in the novel process are aliphatic alpha, omega-dinitriles of the general formula I

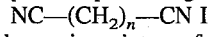
NC—$(CH_2)_n$—CN  I where n is an integer from 1 to 10, in particular 2, 3, 4, 5 or 6. Particularly preferred compounds I are succinonitrile, glutaronitrile, adiponitrile, pimelonitrile and suberonitrile, very particularly preferably adiponitrile.

In the novel process, the dinitriles I described above are partially hydrogenated in the presence of a solvent using a catalyst to give alpha, omega-aminonitriles of the general formula II

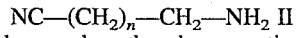
NC—$(CH_2)_n$—$CH_2$—$NH_2$  II where n has the abovementioned meanings. Particularly preferred aminonitriles II are those in which n is 2, 3, 4, 5 or 6, in particular 4, ie. 4-aminobutyronitrile, 5-aminopentanenitrile, 6-aminohexanenitrile (6-aminocapronitrile), 7-aminoheptanenitrile and 8-aminooctanenitrile, very particularly preferably 6-aminocapronitrile.

If the reaction is carried out in a suspension, temperatures of from 40° to 150° C., preferably from 50° to 100° C., particularly preferably from 60° to 90° C., are usually chosen; the pressure is chosen in general to be from 2 to 20, preferably from 3 to 10, particularly preferably from 4 to 9, MPa. The residence times are essentially dependent on the desired yield and selectivity and on the desired conversion; usually, the residence time is chosen so that a maximum yield is obtained, for example from 50 to 275, preferably from 70 to 200, minutes when adiponitrile is used.

In the suspension procedure, preferably used solvents are ammonia, amines, diamines and triamines of 1 to 6 carbon atoms, such as trimethylamine, triethylamine, tripropylamine and tributylamine, or alcohols, in particular methanol and ethanol, particularly preferably ammonia. A dinitrile concentration of from 10 to 90, preferably from 30 to 80, particularly preferably from 40 to 70%, by weight, based on the sum of dinitrile and solvent, is advantageously chosen.

The amount of catalyst is chosen in general so that the amount of catalyst is from 1 to 50, preferably from 5 to 20%, by weight, based on the amount of dinitrile used.

The suspension hydrogenation can be carried out batchwise or, preferably, continuously, as a rule in the liquid phase.

The partial hydrogenation can also be carried out batchwise or continuously in a fixed-bed reactor by the trickle-bed or liquid-phase procedure, a temperature of from 20° to 150° C., preferably from 30° to 90° C., and a pressure of, as a rule, from 2 to 30, preferably from 3 to 20, MPa generally being chosen. According to the invention, the partial hydrogenation is carried out in the presence of a solvent, preferably ammonia, amines, diamines and triamines of 1 to 6 carbon atoms, such as trimethylamine, triethylamine, propylamine and tributylamine, or alcohols, preferably methanol and ethanol, particularly preferably ammonia. In a preferred embodiment, an ammonia content of from 1 to 10, preferably from 2 to 6, g per g of adiponitrile is chosen. A catalyst space velocity of from 0.1 to 2.0, preferably from 0.3 to 1.0, kg of adiponitrile per l per h is chosen. The conversion and hence the selectivity can be controlled by changing the residence time in this case too.

In the novel process, alpha, omega-aminonitriles are obtained in good selectivities and with only small amounts of hexamethylenediamine. Furthermore, the catalysts used according to the invention have a substantially longer life than comparable prior art catalysts. The alpha, omega-aminonitriles are important starting compounds for the preparation of cyclic lactams, in particular 6-aminocapronitrile for caprolactam.

EXAMPLES

Comparative Example 1: (Example 2 in DE-A 848,654)

A tube reactor having a length of 4.5 m and an internal diameter of 0.6 cm was filled with 105 ml (96 g) of catalyst consisting of 2.3% by weight of PdO on $SiO_2$ (remainder), and the catalyst was then activated at atmospheric pressure in the course of 48 hours in a stream of hydrogen (200 l/h) by increasing the temperature from 30° C. to 250° C. After the temperature had been reduced to 120° C., a mixture of 55 ml/h of adiponitrile (ADN), 130 ml/h of ammonia and 200l/h of hydrogen was fed to the reactor at 180 bar. Under these conditions, 13% of the adiponitrile were converted. The reaction mixture consisted essentially of 87% by weight of ADN and 3.3% by weight of ACN (6-aminocapronitrile). Under these conditions, the catalyst lost 3% of its initial activity per hour of operation.

Comparative Example 2: (Example 4 in DE-A 848,654)

Using 4% by weight of CuO, 4% by weight of ZnO and 16.6% by weight of $CO_2O_3$ on $SiO_2$ (remainder) as the catalyst, a mixture of 55 ml/h of adiponitrile, 130 ml/h of ammonia and 200 l/h of hydrogen was reacted to a conversion of 50% at 80° C. and 180 bar in the same reactor as in Comparative Example 1. The reacted mixture consisted of 50% by weight of ADN, 40% by weight of ACN and 9% by weight of HMD (hexamethylenediamine). By increasing the reaction temperature to 95° C., the conversion increased to 69%. The reaction mixture consisted essentially of 31% by weight of ADN, 46% by weight of ACN and 21% by weight of HMD. Under these conditions, the catalyst lost 1% of its initial activity per hour of operation, and the moldings had completely disintegrated after 60 hours.

Comparative Example 3: (Example 3 in DE-A 848,654)

Using 7.5% by weight of CoO and 16% by weight of $Fe_2O_3$ on $SiO_2$ (remainder) as a catalyst, a mixture of 55 ml/h of adiponitrile, 130 ml/h of ammonia and 200 l/h of hydrogen was reacted to a conversion of 45% at 70° C. and 180 bar in the same reactor as in Comparative Example 1. The reacted mixture consisted essentially of 55% by weight of ADN, 37% by weight of ACN and 7% by weight of HMD. By increasing the reaction temperature to 85° C., the conversion increased to 78%. The reaction mixture consisted essentially of 22% by weight of ADN, 48% by weight of ACN and 27% by weight of HMD. The catalyst lost 0.5% of its initial activity per hour of operation, and 10% of its initial activity in the course of 24 hours.

Example 1

A tube reactor having a length of 2 m and an internal diameter of 2.5 cm was filled with 750 ml (1534 g) of catalyst consisting of 90% by weight of CoO, 5% by weight of $Mn_2O_3$, 3% by weight of $P_2O_5$ and 2% by weight of $Na_2O$, and the catalyst was then activated at atmospheric pressure in the course of 48 hours in a stream of hydrogen (500 l/h) by increasing the temperature from 30° C. to 280° C. After the temperature had been decreased to 60° C., a mixture of 400 ml/h of adiponitrile, 930 ml/h of ammonia and 500 l/h of hydrogen was fed to the reactor at 200 bar. Under these conditions, 46% of adiponitrile were converted. The reaction mixture consisted essentially of 54% by weight of ADN, 37% by weight of ACN and 9% by weight of HMD. By increasing the reaction temperature to 70° C., the conversion increased to 65%. The reaction mixture consisted essentially of 34.5% by weight of ADN, 46% by weight of ACN and 19.5% by weight of HMD. After 900 hours, the catalyst still had the same selectivity as fresh catalyst, the acti-vity being unchanged. The catalyst moldings were still intact after removal (after 900 hours).

Example 2

A tube reactor having a length of 4.5 m and an internal diameter of 0.6 cm was filled with 105 ml (96 g) of catalyst consisting of 20% by weight of CoO, 5% by weight of $Mn_2O_3$, 0.3% by weight of $Ag_2O$, 70% by weight of $SiO_2$, 3.5% by weight of $Al_2O_3$, 0.4% by weight of $Fe_2O_3$, 0.4% by weight of MgO and 0.4% by weight of CaO, and the catalyst was then activated at atmospheric pressure in the course of 48 hours in a stream of hydrogen (200 l/h) by increasing the temperature from 30° C. to 250° C. After the temperature had been decreased to 90° C., a mixture of 55 ml/h of adiponitrile, 130 ml/h of ammonia and 200 l/h of hydrogen was fed to the reactor at 180 bar. Under these conditions, 30% of the adiponitrile were converted. The reaction mixture consisted essentially of 65% by weight of ADN, 30% by weight of ACN and 4% by weight of HMD. By increasing the reaction temperature to 100° C., the conversion increased to 71%. The reaction mixture consisted essentially of 29% by weight of ADN, 53% by weight of ACN and 18% by weight of HMD. After 300 hours, the catalyst still had the same selectivity as fresh catalyst, the activity being unchanged.

Example 3

A tube reactor having a length of 4.5 m and an internal diameter of 0.6 cm was filled with 105 ml (96 g) of catalyst consisting of 20.0% by weight of NiO, 67.42% by weight of $SiO_2$, 3.7% by weight of $Al_2O_3$, 0.8% by weight of $Fe_2O_3$, 0.76% by weight of MgO, 1.92% by weight of CaO, 3.4% by weight of $Na_2O$ and 2.0% by weight of $K_2O$, and the catalyst was then activated at atmospheric pressure in the course of 48 hours in a stream of hydrogen (200 l/h) by increasing the temperature from 30° C. to 250° C. After the temperature had been decreased to 110° C., a mixture of 50 ml/h of adiponitrile, 130 ml/h of ammonia and 200 l/h of hydrogen was fed to the reactor at 180 bar. Under these conditions, 25% of the adiponitrile were converted. The reaction mixture consisted essentially of 75% by weight of ADN, 24% by weight of ACN and 0.5% by weight of HMD. By increasing the reaction temperature to 120° C., the conversion increased to 60%. The reaction mixture consisted essentially of 40% by weight of ADN, 53% by weight of ACN and 5% of HMD. The catalyst had a constant activity over 100 hours.

We claim:

1. A process for the preparation of aliphatic alpha, omega-aminonitriles of the formula II NC—$(CH_2)_n$—CH—$NH_2$ 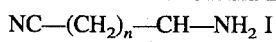 I where n is an integer from 1 to 10, by partial hydrogenation of aliphatic alpha-omega-dinitriles at elevated temperature and superatmospheric pressure in the presence of a solvent and of a catalyst, which comprises carrying out the partial hydrogenation in the presence of a catalyst which (a) contains cobalt and
(b) contains from 0.01 to 25% by weight, based on (a), of a promoter based on a metal selected from the group consisting of palladium, platinum, iridium, osmium, iron, copper, silver, gold, chromium, molybdenum, tungsten, manganese, rhenium, zinc, cadmium, lead, aluminum, tin, phosphorus, arsenic, antimony, bismuth and rare earth metals and
(c) from 0 to 5% by weight, based on (a), of a trace component based on a metal selected from the group consisting of an alkali metal and an alkaline earth metal, said catalyst being obtained by (I) precipitating precursors of the components (a) to (c) from aqueous solutions in the presence or absence of carriers yielding a precipitate,
(II) optionally processing the resulting precipitate to give extrudates or pellets,
(III) drying the precipitate or pellets or extrudates at a temperature from 80° to 150° C. yielding a dried product, and
(IV) calcining the dried product at a temperature from 150° to 500° C. in a gas stream comprising air or nitrogen yielding a calcined product, then
(V) optionally passivating the surface of the calcined product at from 20° to 80° C. by means of an oxygen/nitrogen mixture yielding a passivated product, then (VI) activating the calcined or passivated product by exposing it to a reducing atmosphere for from 2 to 24 hours at from 200° to 500° C.

2. The process of claim 1, wherein the catalyst is a supported catalyst.

3. The process as claim 1, wherein the catalyst is an unsupported catalyst.

4. The process of claim 1, wherein the hydrogenation is carried out in a suspension.

5. The process of claim 1, wherein the hydrogenation is carried out in a fixed-bed reactor.

6. The process of claim 1, wherein the alpha, omega-dinitrile used is adiponitrile, 6-aminocapronitrile being obtained.

7. The process of claim 6, wherein the hydrogenation is carried out at from 2 to 40 MPa.

8. The process of claim 6, wherein the hydrogenation is carried out at from 30° to 150° C.

* * * * *

UNITED STATES PATENT AND TRADEMARK OFFICE
CERTIFICATE OF CORRECTION

PATENT NO.: 5,527,946

DATED: June 18, 1996

INVENTOR(S): FLICK et al.

It is certified that error appears in the above-identified patent and that said Letters Patent is hereby corrected as shown below:

Column 6, claim 1, line 36, "NC-$(CH_2)_n$-CH-$NH_2$" should read --NC-$(CH_2-)_n$-$CH_2$-$NH_2$--; line 36, "I" should read --II--.

Signed and Sealed this

Fourteenth Day of January, 1997

Attest:

BRUCE LEHMAN

*Attesting Officer*  *Commissioner of Patents and Trademarks*